United States Patent
Fornaroli et al.

(10) Patent No.: US 6,667,420 B2
(45) Date of Patent: Dec. 23, 2003

(54) PROCESS FOR THE PREPARATION OF SODIUM DIVALPROATE

(75) Inventors: Mirco Fornaroli, Cameri (IT); Francesco Velardi, Cameri (IT)

(73) Assignee: Procos SpA, Cameri (IT)

( * ) Notice: Subject to any disclaimer, the term of this patent is extended or adjusted under 35 U.S.C. 154(b) by 0 days.

(21) Appl. No.: 10/179,246

(22) Filed: Jun. 26, 2002

(65) Prior Publication Data

US 2003/0018215 A1 Jan. 23, 2003

(30) Foreign Application Priority Data

Jun. 29, 2001 (IT) ..................................... MI2001A1379

(51) Int. Cl.$^7$ ................................................ C07B 53/00
(52) U.S. Cl. ....................................................... 562/606
(58) Field of Search ......................................... 562/606

(56) References Cited

FOREIGN PATENT DOCUMENTS

CA          1144558 A    *    4/1983

\* cited by examiner

Primary Examiner—Johann Richter
Assistant Examiner—Paul A. Zucker
(74) Attorney, Agent, or Firm—Young & Thompson

(57) ABSTRACT

A process for the preparation of sodium divalproate by reacting valproic acid and sodium methoxide in an inert solvent, azeotropically removing the formed methanol.

5 Claims, No Drawings

PROCESS FOR THE PREPARATION OF SODIUM DIVALPROATE

The present invention relates to a process for the preparation of sodium divalproate.

Valproic acid and its sodium salt have been used for some time as anticonvulsant drugs, particularly in the treatment of epilepsy attacks and convulsive seizures.

Both drugs can, however, involve formulation problems, because the acid is in the liquid form, while the sodium salt is a hygroscopic solid and has therefore poor stability; furthermore, its formulation causes problems, well known to those skilled in the art whenever dealing with hygroscopic materials. Therefore, attempts have been made to prepare a valproic acid derivative having such better characteristics as to allow an easy formulation in suitable pharmaceutical forms.

As a result of such attempts, sodium divalproate, of formula (I)

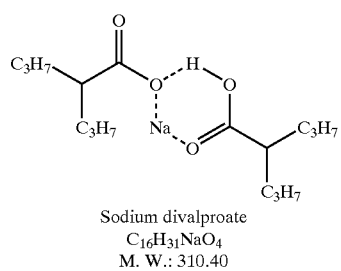

Sodium divalproate
$C_{16}H_{31}NaO_4$
M. W.: 310.40 which is a complex, non hygroscopic salt, having remarkable stability, has been developed.

However, the processes at present known (see, for example, PCT/US80/00954) for the preparation of this salt start from sodium valproate, whose above mentioned hygroscopicity involves production problems, in that it can adversely affect the chemical and microbiological stability, thus leading to problems in terms of preservation. The presence of high relative humidity can, in fact, even make mould growth possible. It is therefore evident that a process using such highly hygroscopic starting material as sodium valproate is not ideal from the industrial point of view.

It has now been found, and it is the object of the present invention, a process for the preparation of sodium divalproate, which does not use the valproic acid sodium salt as starting material.

According to the present invention, sodium divalproate is in fact prepared starting from valproic acid and sodium methoxide, according to the following reaction scheme:

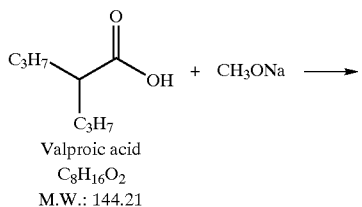

Valproic acid
$C_8H_{16}O_2$
M.W.: 144.21

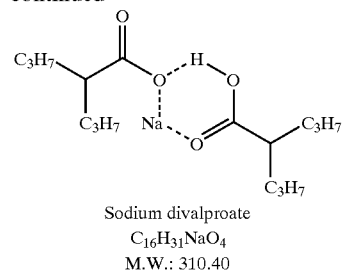

Sodium divalproate
$C_{16}H_{31}NaO_4$
M.W.: 310.40

The reaction is carried out in hydrocarbon solvents, such as heptane, hexane, ligroin and the like. The valproic acid to sodium methoxide molar ratio can range from 2.5 to 0.8, and is more preferably 2:1.

The methanol formed during the reaction is removed by azeotropical distillation, after that any insoluble impurities are filtered off and the salt is recovered by concentration to dryness and melting to about 110–120° C. The molten mass is then cooled to about 60° C. and crystallized from acetone or diisopropyl ether to obtain extremely pure sodium divalproate.

The process of the present invention is illustrated in greater detail in the following example.

EXAMPLE

A 2 l round-bottom flask, equipped with mechanical stirrer, thermometer and Dean-Stark condenser, is loaded with:

| | |
|---|---|
| Heptane | 500 ml |
| Sodium methoxide | 81.8 g |
| | (1.505 mols) |
| After that | |
| valproic acid | 437 g |
| | (3.03 mols) | is slowly added (exothermic reaction).

The mixture is refluxed, and the formed methanol is azeotropically removed. In case the resulting solution is turbid, it is filtered at 60–70° C. If the solution is coloured, it may be treated with active charcoal.

The clear solution is evaporated to dryness under vacuum, then the mass is melted at 110–120° C. The chemical titre is calculated in double (with NaOH and $HClO_4$) on a sample, to evaluate the reaction balance (titres should be complementary to 200 and fall within the range 98–102%, otherwise they should be balanced by addition of valproic acid and sodium methoxide, repeating the azeotropical distillation from the start).

The mass is cooled to 60° C. and dissolved by refluxing in

| | |
|---|---|
| Acetone | 940 ml |

After cooling to 40° C. and seeding with the crystalline product, the mixture is slowly cooled overnight. Afterwards, it is cooled to 0° C. and kept at this temperature for an hour, then filtered and washed with some acetone cooled at 0° C. The resulting product is dried at 40° C. under vacuum, to obtain 414 g of dry product.

Chemical titre (NaOH): 99.5%
Chemical titre (HClO$_4$): 101.5%
Yield: 88.3%

What is claimed is:

1. A process for the preparation of sodium divalproate, of formula (I):

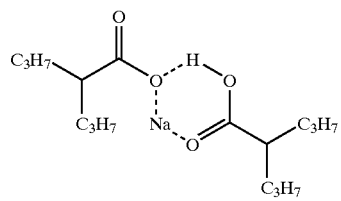

characterized in that valproic acid is reacted with sodium methoxide, according to the following scheme:

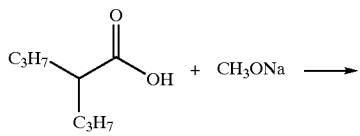

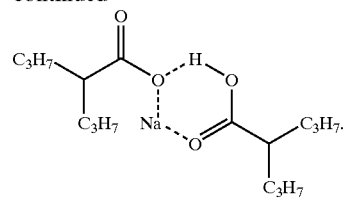

2. A process as claimed in claim 1, characterized in that the valproic acid to sodium methoxide molar ratio is about 2:1.

3. A process as claimed in claim 1, characterized in that said process is carried out in a hydrocarbon solvent.

4. A process as claimed in claim 3, characterized in that the hydrocarbon solvent is heptane.

5. A process as claimed in claim 2, characterized in that said process is carried out in a hydrocarbon solvent.

* * * * *